(12) United States Patent
Snyder

(10) Patent No.: US 6,658,291 B2
(45) Date of Patent: *Dec. 2, 2003

(54) ELECTRODE SYSTEM FOR IMPROVED DETECTION OF PAD CONTACT AND ARTIFACT DETECTION OR REMOVAL

(75) Inventor: David E Snyder, Bainbridge Island, WA (US)

(73) Assignee: Koninklijke Philips Electronics N.V., Eindhoven (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/288,581

(22) Filed: Apr. 8, 1999

(65) Prior Publication Data

US 2001/0051821 A1 Dec. 13, 2001

(51) Int. Cl.[7] .................................................. A61N 1/39
(52) U.S. Cl. ............................................. 607/8; 607/142
(58) Field of Search ................................. 607/142, 145, 607/115, 148, 152, 7, 8, 28; 600/372, 393

(56) References Cited

U.S. PATENT DOCUMENTS

| 4,419,998 A |   | 12/1983 | Health |
|---|---|---|---|
| 4,483,103 A |   | 11/1984 | Bickel |
| 4,653,503 A |   | 3/1987 | Health |
| 4,681,112 A |   | 7/1987 | Jones et al. |
| 4,807,621 A | * | 2/1989 | Hagen et al. ............... 607/142 |
| 4,852,585 A |   | 8/1989 | Heath |
| 4,895,169 A |   | 1/1990 | Heath |
| 4,955,381 A |   | 9/1990 | Way et al. |
| 4,979,517 A |   | 12/1990 | Grossman et al. |
| 5,080,099 A |   | 1/1992 | Way et al. |
| 5,137,458 A |   | 8/1992 | Ungs et al. |
| 5,295,482 A | * | 3/1994 | Clare et al. ................ 607/142 |
| 5,330,526 A |   | 7/1994 | Fincke et al. |
| 5,352,315 A |   | 10/1994 | Carrier et al. |
| 5,466,244 A |   | 11/1995 | Morgan |
| 5,520,683 A | * | 5/1996 | Subramaniam et al. ..... 607/142 |
| 5,571,165 A |   | 11/1996 | Ferrari |
| 5,617,853 A | * | 4/1997 | Morgan ...................... 607/142 |

OTHER PUBLICATIONS

"Improving Survival from Sudden Cardiac Arrest: The 'Chain of Survival' Concept" Circulation 83:1832–1847 (1991).

* cited by examiner

*Primary Examiner*—George R. Evanisko

(57) ABSTRACT

This invention relates generally to medical electrode systems. In particular, the electrodes of this invention are capable of delivering synchronized cardioversion energy pulses as well as defibrillation energy pulses to a patient. The electrodes of this invention are appropriate for use with an automatic or semi-automatic external defibrillator ("AED") as well as defibrillators capable of cardioversion. At least one electrode in an electrode set has a substrate with an adhesive surface, and conductors in communication with the substrate. The electrode further has a plurality of conductive elements electrode elements disposed on a substrate wherein each electrode element is in a spatial relationship to each other and electrically connected to the conductors, further the spatial relationship of the conductors facilitates the determination of an overall electrode pad attachment quality. A method of using the electrodes of this invention is also described.

4 Claims, 5 Drawing Sheets

ELECTRODE SYSTEM FOR IMPROVED DETECTION OF PAD CONTACT AND ARTIFACT DETECTION OR REMOVAL

BACKGROUND OF THE INVENTION

1. Field of the Invention

This invention relates generally to medical electrode systems. In particular, the electrodes of this invention are capable of delivering synchronized cardioversion energy pulses as well as defibrillation energy pulses to a patient. The electrodes of this invention are appropriate for use with an automatic or semi-automatic external defibrillator ("AED") as well as defibrillators capable of cardioversion.

2. Description of the Prior Art

Cardiac arrhythmias treatable with an electric shock can be further categorized as arrhythmias treated by a defibrillation energy shock or arrhythmias treated by a synchronized cardioversion energy shock. Electric shocks are typically delivered by defibrillators or cardioverters. Many devices capable of delivering a defibrillation shock are also capable of delivering synchronized cardioversion shocks. Defibrillation is typically used to treat ventricular fibrillation ("VF") and pulseless ventricular tachycardia ("VT"), while cardioversion is typically used to treat hemodynamically stable ventricular tachycardia ("VT" with pulse), paroxysmal supraventricular tachycardia ("PSVT"), atrial fibrillation ("AF") and atrial flutter. More detailed information about electrocardiography and the various types of heart rhythms may be obtained from Wagner "Marriott's Practical Electrocardiography," 9th Ed. (1994).

One frequent consequence of heart attacks is the development of cardiac arrest associated with heart arrhythmias, such as VF. This abnormal heart rhythm is caused by an abnormal and chaotic electrical activity in the heart. During VF the heart cannot pump blood effectively. VF is treated by applying a defibrillation shock to the patient's heart through the use of a defibrillator. Defibrillation clears the heart of the abnormal electrical activity and allows the heart's natural pacemaker areas to restore normal function. Because blood is no longer pumping effectively during VF, the chance of surviving a heart attack decreases with time after the arrest. Quick response to a heart attack by administering a defibrillating shock as soon as possible after the onset of VF is therefore often critically important.

VT is an arrhythmia originating in the ventricles, and is usually defined as having a heart rate of >100 beats/minute in an adult. VT can result in a significant health risk, since the ability of the heart to pump adequate blood is compromised. As a result, blood pressure falls. The amount of time VT can be tolerated by a patient depends on the condition of the patient and the nature of the VT, and could range from minutes to hours or days. Hemodynamically stable VT is typically treated using synchronized energy pulses known as cardioversion that are delivered in a standard sequence of, for example, 100, 200, 300 and 360 J. Although in some situations, pulses may begin with as little as 50 J. Hemodynamically unstable VT is typically treated with unsynchronized shocks. The most current protocol information can be obtained from the American Heart Association ("AHA"). The protocol information described herein can be found in "Improving Survival from Sudden Cardiac Arrest: The 'Chain of Survival' Concept" *Circulation* 83:1832–1847 (1991).

Increasing the number of potential defibrillator operators who are trained on the proper use of an external defibrillator increases the likelihood that a trained defibrillator operator will be available during an emergency and thus could ultimately reduce the time to defibrillator deployment. As the number of potential operators increases, however, it becomes increasingly important to ensure that the defibrillator electrodes are adequately attached so that the device can receive and accurately analyze a heart rhythm signal. Accordingly, it is important to be able detect how well an electrode is attached so that the quality of therapy can be maximized, and so that electrode burns can be minimized. Traditionally, the need for detecting correct electrode attachment is balanced with the importance for quick response.

Another problem that occurs is that, inexperienced operators are more likely to fumble around in attempting to attach the electrode pads to the patient. This fumbling creates a mechanical disturbance that can result in a non-cardiac event signal being transmitted to the defibrillator along with the ECG signal of interest. As will be appreciated by those of skill in the art, signals from a mechanical disturbance are just one type of artifact signal that can corrupt the ECG signal of interest. If the ECG signal has been corrupted by artifact and the corruption is not detected and/or removed, this could result in the signal being misinterpreted. The less clinical judgment possessed by the user, the more important accurate artifact detection and/or removal becomes. Thus, as devices continue to move into the hands of lay responders, it becomes critically important that the device be able to anticipate and respond to situations where the user inadvertently creates artifact, such as a mechanical disturbance, or fails to correctly attach the electrode. None of the commercially available defibrillation or pacing electrodes are designed to address this problem. Further since the functionality of such electrodes is known in the art it will not be described herein.

What is needed is an electrode that enables the defibrillator to quickly and accurately detect and/or remove artifact from the patient and/or assess quality of pads attachment to assure optimal therapy delivery.

SUMMARY OF THE INVENTION

This invention provides a medical electrode system wherein the electrode pads are capable of improved detection of electrode attachment and improved artifact detection. Each electrode pad has a flexible substrate with an adhesive surface; two or more conductors disposed on the substrate; and two or more electrode elements disposed on the substrate and electrically connected to the conductors.

In a first embodiment, a medical electrode pad is provided. The medical electrode pad comprises a substrate with an adhesive surface; conductors in communication with the substrate; and a plurality of conductive electrode elements disposed on the substrate in a spatial relationship to each other and electrically connected to the conductors, wherein the spatial relationship of the conductors facilitates the determination of an overall electrode pad attachment quality.

In a second embodiment, the conductive electrode elements of the electrode pad may be formed so that an estimate of the degree of electrode pad contact on a patient can be calculated based on the measurement of resistance between a set of at least two of the conductive electrode pad elements. Additionally, the conductive electrode elements may be used to estimate the degree of electrode pad contact and may have an annular spatial relationship to each other. Importantly, the conductive electrode elements would be formed so that a patient skin resistivity can be calculated, independent of the degree of electrode pad contact, based on the measurement of resistance between a second set of at least two of the conductive electrode pad elements, wherein the skin resistivity is used to refine the estimate of the degree of electrode pad contact on a patient. In accomplishing the calculation of skin resistivity, the conductive electrode elements could have an annular spatial relationship to each other.

In a third embodiment, the conductive electrode elements of the electrode pad are formed so that an estimate of the degree of electrode pad contact on a patient can be calculated based on the measurement of conductance between a set of at least two of the conductive electrode pad elements. The conductive electrode elements have an annular spatial relationship to each other and are used to estimate the degree of the electrode pad contact. The conductive electrode elements could be formed so that a patient skin conductivity can be calculated, independent of the degree of electrode pad contact, based on the measurement of conductance between a second set of at least two of the conductive electrode pad elements. The skin conductivity is then used to refine the estimate of the degree of electrode pad contact on a patient. The conductive electrode elements used to calculate the patient skin conductivity may have an annular spatial relationship to each other.

In a fourth embodiment of the invention, the conductive electrode elements are formed so that an artifact reference signal can be detected based on the measurement of a differential voltage between a set of at least two of the conductive electrode pad elements.

Several methods may be employed to operate the invention. In a first method of the invention, the electrode pad of the invention is used by: applying an electrode pad having a plurality of conductive electrode elements to a patient; and then determining a pad attachment quality for an electrode pad based on a measured resistance between a first and second conductive element, the gap width between the first and second conductive electrode element, the effective perimeter of the gap between the second and third electrode element, and a typical skin resistivity value.

In a second method of using the invention, a medical electrode pad is used by: applying an electrode pad having a plurality of conductive electrode elements to to a patient; calculating a patient's local skin resistivity based on a measured resistance between a first and second conductive element, the gap width between the first and second conductive electrode element, and the effective perimeter of the gap between the first and second electrode element; and then determining a pad attachment quality for an electrode pad based on the local skin resistivity so calculated, the gap width between a third and fourth conductive electrode element, the measured resistance between the third and fourth conductive element and the effective perimeter of the gap between the third and fourth electrode element. Further, one of the first and second electrode elements, and one of the third and fourth electrode elements could comprise the same element.

In a third method of using the invention, a medical electrode pad is used by: applying an electrode pad having a plurality of conductive electrode elements to a patient; and then determining a pad attachment quality for an electrode pad based on a measured conductance between a first and second conductive element, the gap width between the first and second conductive electrode element, the effective perimeter of the gap between the second and third electrode element, and a typical skin conductivity value.

In a fourth method of using the invention, a medical electrode pad is used by: applying an electrode pad having a plurality of conductive electrode elements to a patient; calculating a patient's local skin conductivity based on a measured conductance between a first and second conductive element, the gap width between the first and second conductive electrode element, and the effective perimeter of the gap between the first and second electrode element; and then determining a pad attachment quality for an electrode pad based on the local skin conductivity so calculated, the gap width between a third and fourth conductive electrode element, the measured conductance between the third and fourth conductive element and the effective perimeter of the gap between the third and fourth electrode element. Further, one of the first and second electrode elements, and one of the third and fourth electrode elements could comprise the same element.

In a fifth method of using the invention, a medical electrode pad is used by: applying an electrode pad having a plurality of conductive electrode elements to a patient; and then calculating an artifact reference signal based on a differential voltage value between at least two of the plurality of conductive electrode elements.

Other features and advantages of the invention will be apparent from the following description of the preferred embodiments, and from the claims.

DESCRIPTION OF THE PREFERRED EMBODIMENTS

As used herein "electrode pad" refers to the completed electrode pad assembly that is attached to the patient. Further, "conductive electrode elements," "conductive elements", "electrode elements" and "elements" refer to the sub-components forming the conductive components of the electrode pad.

Figure 1:
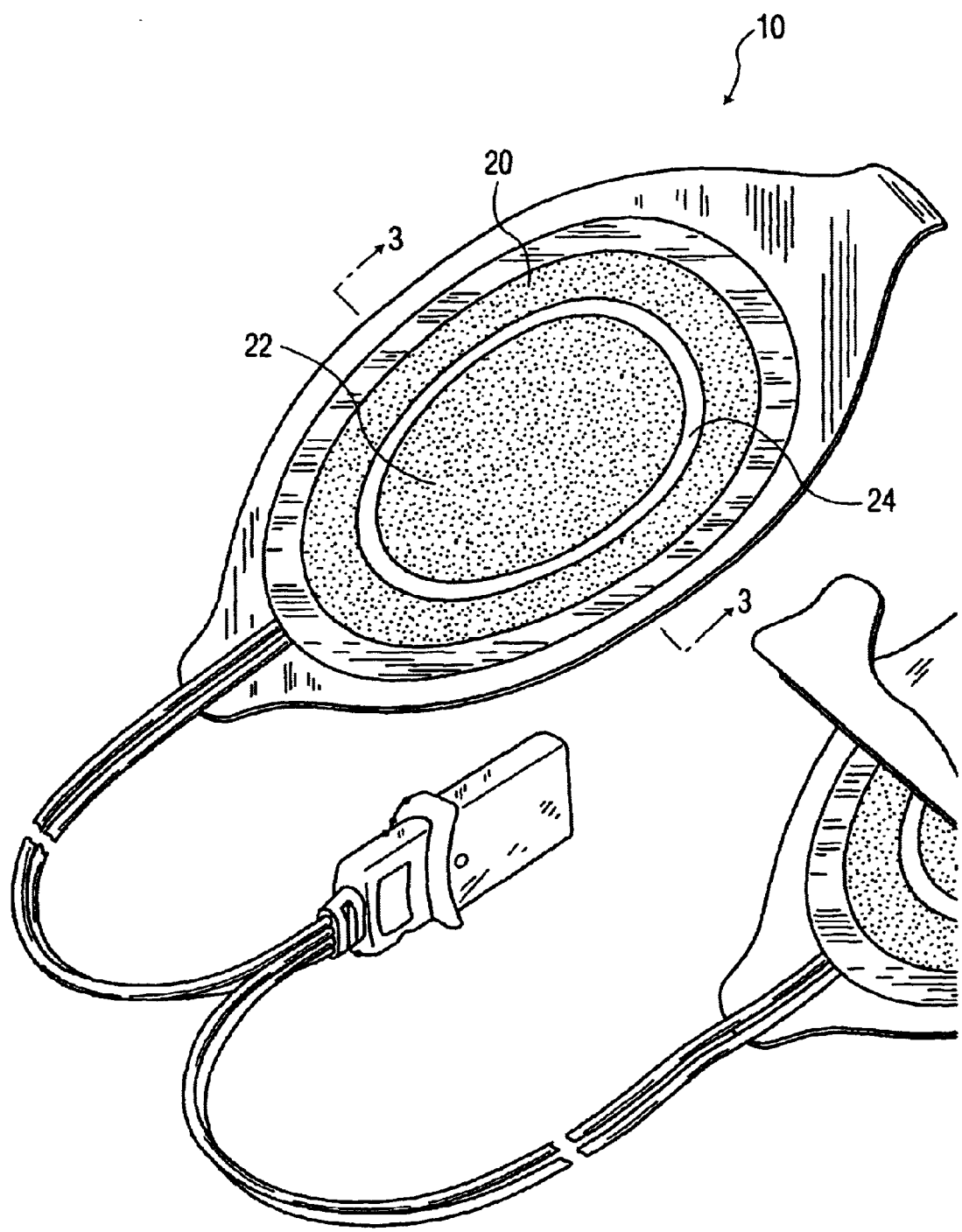
FIG. 1 is a bottom elevational view of an electrode system according to a preferred embodiment of this invention wherein the electrode has two conductive elements, one comprising an annulus about the other.

FIG. 1. Is a bottom elevational view of an electrode configuration according to a preferred embodiment of this invention. As shown in FIG. 1, the electrode 10 has a pair of conductive electrode elements 20, 22, together comprising a conductive contact area of 80 to 160 $cm^2$, more preferably 115 $cm^2$. The conductive elements 20, 22 are separated by a gap 24. In a preferred embodiment, the gap 24 has an approximately constant width and comprises an area smaller than the combined areas of the conductive electrode elements 20, 22; the gap area being, for example, 5 to 25% of the total combined surface areas of the conductive electrode elements 20, 22.

In the embodiment shown in FIG. 1, the outer conductive element 20 forms an annular ring with a surface area smaller than that of the inner conductive element 22. In a preferred embodiment, the surface area of the outer annular ring is from 5 to 25% of the total combined surface area of the conductive elements 20, 22, and more preferably 15% of the total conductive surface area. In the embodiment shown in FIG. 1, the inner conductive element 22 may be used alone, or in cooperation with the outer conductive element 20 to deliver defibrillation or pacing energy.

In an alternative embodiment, the outer conductive element 20 may comprise an area greater than that of the inner conductive element 22. This result would occur when, for example, a construction such as that depicted in FIG. 4 (which is discussed in more detail below) is employed. In that case, the outer conductive electrode element may be used alone, or in cooperation with the inner conductive element to deliver defibrillation or pacing energy to the patient.

In operation, the electrode 10 of FIG. 1 enables an operator to detect the relative degree of electrode pad contact by allowing an admittance (or equivalently impedance) value to be detected between the outer conductive element 20 and the inner conductive element 22. In one experiment, the following values of the real components of the impedance (i.e. resistance, R), and the admittance (i.e. the conductance, G) were obtained using a small signal measurement at 540 Hz:

TABLE 1

RESISTANCE & CONDUCTANCE VS. ATTACHMENT

| Pad Condition | G (mmho) | 1/R (mmho) |
|---|---|---|
| Detached | 0 | 0 |
| 25% attached | 0.110 | 0.58 |
| 50% attached | 0.178 | 1.06 |
| 75% attached | 0.302 | 1.75 |
| 100% attached | 0.341 | 2.00 |

These results demonstrate, with either measure, a sensitive and linear measurement of electrode pad attachment which is independent of the transthoracic impedance.

Figure 2:
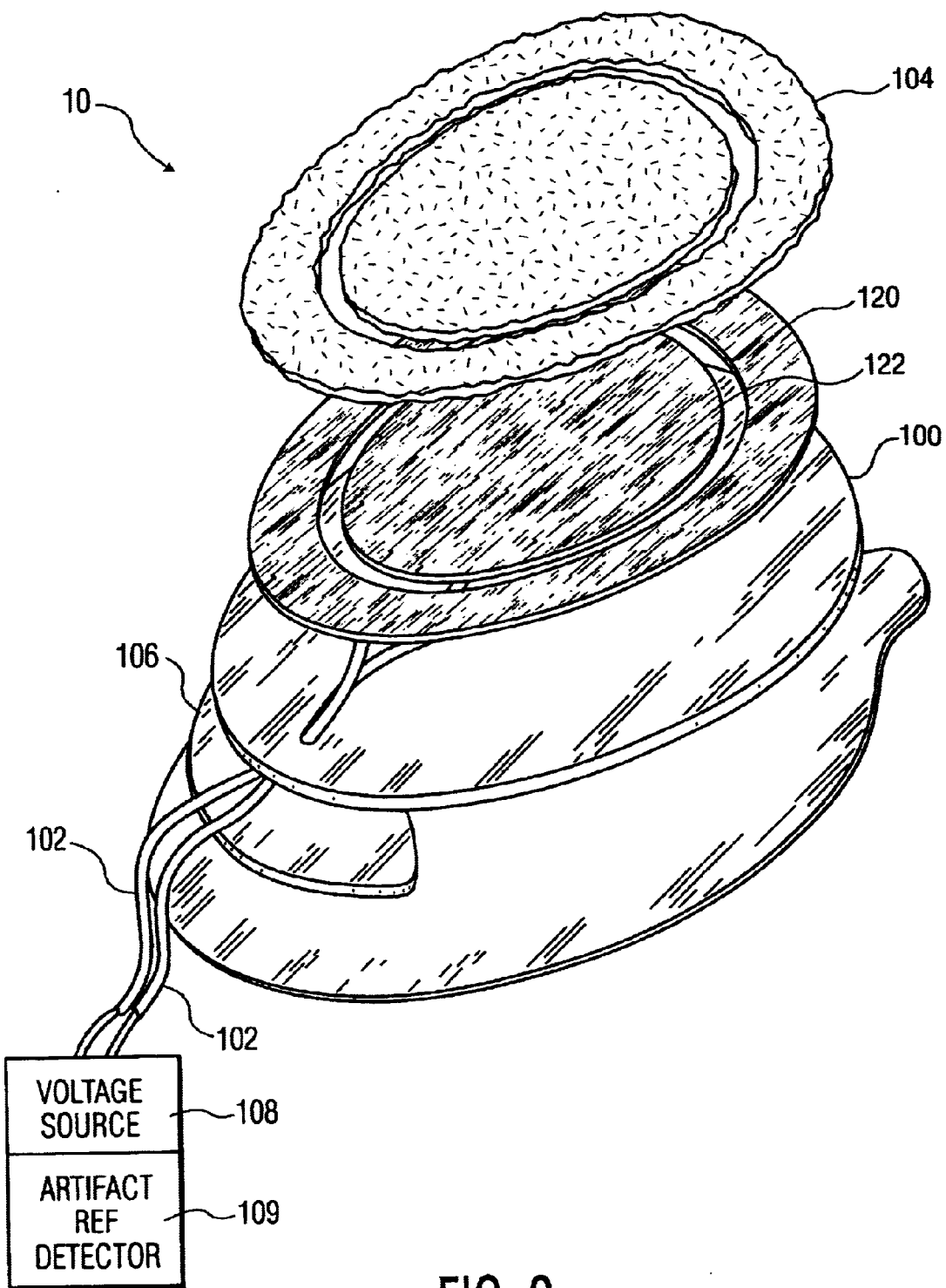
FIG. 2 is an expanded bottom elevational view of the electrode system of FIG. 1.

FIG. 2 shows an expanded bottom elevational view of the electrode of FIG. 1. In this embodiment, the electrode pad 10, is formed of a substrate, such as a flexible foam backing 100. The substrate has two conductive electrode elements 120, 122. The electrode elements are formed, for example, from a piece of metal foil, and attached to the substrate with medical grade adhesive. Suitable metal foil would be, for example, 2 mil Tin. The conductive electrode elements 120, 122 are electrically connected to one or more lead wires 102 between the foam backing layer 100 and the conductive electrode elements 120, 122 on the upper surface of the conductive electrode elements 120, 122. The lead wires 102 are connected to a power source 108 for supplying voltage to the conductive electrode island 122 and the conductive electrode 120 and are connected to an artifact reference signal detection means 109 for detecting a voltage difference between the conductive electrode island and the conductive electrode and for determining an electrode pad attachment quality. The lower surface of the conductive electrode elements 120, 122 are each covered with corresponding layers of conductive gel 104, 105. A suitable conductive gel 104, 105 would be, for example, an RG 63T hydrogel. The gap in the gel corresponds to the gap 124 between the conductive electrode elements 120, 122; thus preventing conduction between the electrode elements.

An additional piece of flexible foam 106 may be further provided at the location where the electrical connection 102 attaches to electrode pad 10.

The conductive gel layers 104, 105 of the electrode pad 10 may be attached to the silicone coated side of a releasing surface (not shown).

As will be appreciated by those skilled in the art, the actual construction described above is provided by way of illustration only and should in no way limit the scope of the invention. Although described in terms of a disposable electrode pad, other constructions are possible. It is also contemplated that materials other than those described herein may be used without departing from the scope of the invention. Further it is within the scope of the invention to have a plurality of electrode elements.

Figure 3:
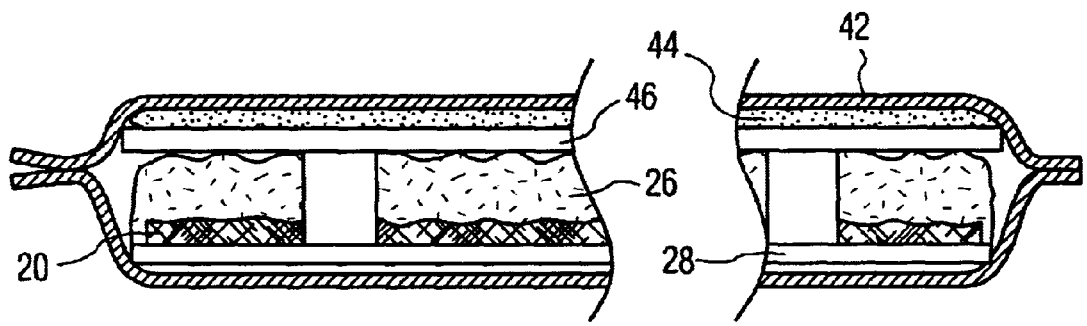
FIG. 3 is a cross-sectional view of the electrode system of FIG. 1 along the lines 3—3.

FIG. 3 shows a cross-section of the electrode shown in FIG. 1 along the lines 3—3, and which is assembled as described above.

Figure 4:
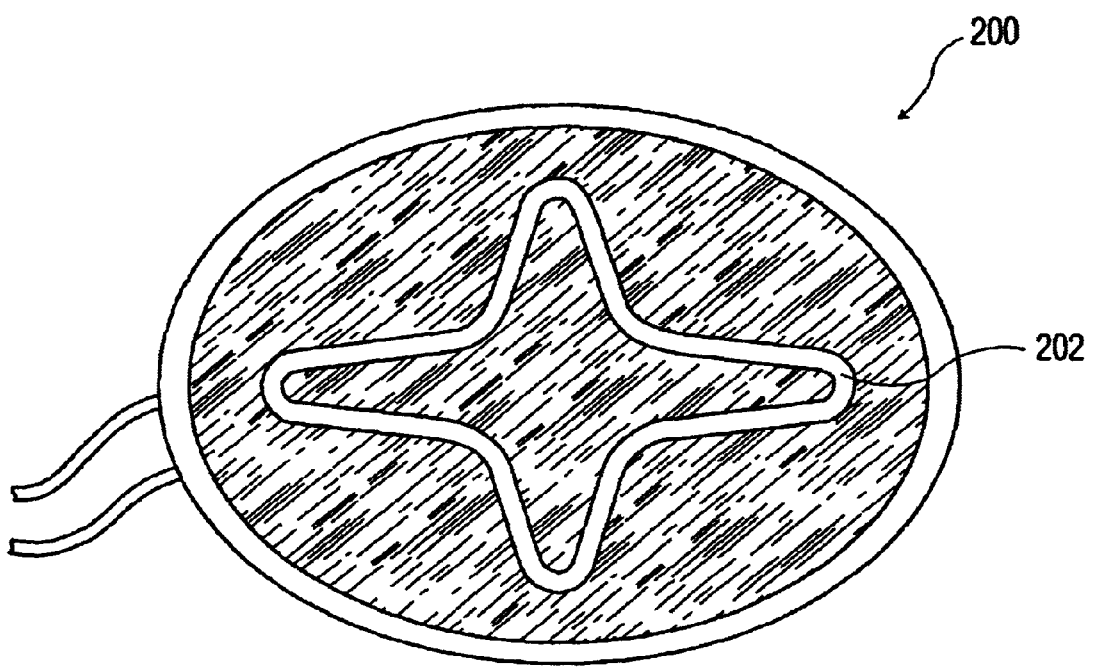
FIG. 4 is a bottom elevational view of an alternative embodiment of an electrode system according to a preferred embodiment wherein the two conductive elements are shaped so that the gap between the conductive areas forms a cross.

FIG. 4 is a bottom elevational view of an alternative embodiment of an electrode 200, according to this invention. The gap 224 between the inner and outer conductive layers 220, 222 is formed in a substantially cross-like shape. The electrode 200 of FIG. 4 is most suited to the delivery of defibrillation energy through the outer electrode element 220 which has the largest surface area, or simultaneously through both electrode elements 220, 222. As will be appreciated by those skilled in the art, other shapes may also be employed to even further increase the conductive area available for the delivery of defibrillation energy. As discussed above, pacing energy pulses used for cardioversion may be delivered using this design as well. As with the delivery of defibrillation energy, pacing pulses are most effectively delivered simultaneously through the all the conductive electrode elements. However, as will be appreciated by those of skill in the art, delivery of pacing energy through the electrode element with the largest surface area would also be effective.

In order to avoid obscuring the invention, the function of electrode pad 10, 200 of FIG. 14, will be discussed in relation to FIG. 4. A person of skill in the art will appreciate that the function will be the same for FIGS. 1–3.

In using the electrode pad, a stored skin resistivity value, $\rho$, is used by the defibrillator to determine the overall electrode pad attachment quality:

Step 1

$$\eta = \frac{\rho W_2}{P_2 R_q}$$

Where $\eta$ is an indication of attachment quality of the electrode pad, $\rho$ is a patient resistivity, such as an average patient resistivity. $R_q$ is a small-signal resistance (real part of impedance) measured between elements 220 and 222. $W_2$ is the gap distance 224 between the electrode element 220 and electrode element 222. $P_2$ is the effective perimeter of the gap 224 between elements 220 and 222 which is a constant value for a given geometry and may be determined either empirically or analytically.

When the electrode pad 200 is deployed for defibrillation, the operator attaches an electrode pad to the patient's torso at each of either the anterior/anterior position or the anterior/posterior position. Thereafter, the defibrillator uses the stored $\rho$ in conjunction with the equation of step 1 to determine whether each electrode pad is attached properly.

As an alternative to the impedance based measurement discussed above, an admittance based measurement can be used. In that instance, a stored skin conductivity, σ, is used. Using the stored σ, the η, which is an indication of attachment quality of the electrode pad, can be calculated:

Step 2

$$\eta = \frac{G_q W_2}{\sigma P_2}$$

Where $G_q$ is the small-signal conductance measured between elements 220 and 222. When the electrode pad 200 is deployed for defibrillation, the operator attaches an electrode pad to the patient's torso at each of either the anterior/anterior position or the anterior/posterior position. Thereafter, the defibrillator uses the stored σ in conjunction with the equation of step 2 to determine whether each electrode pad is attached properly.

Figure 5:
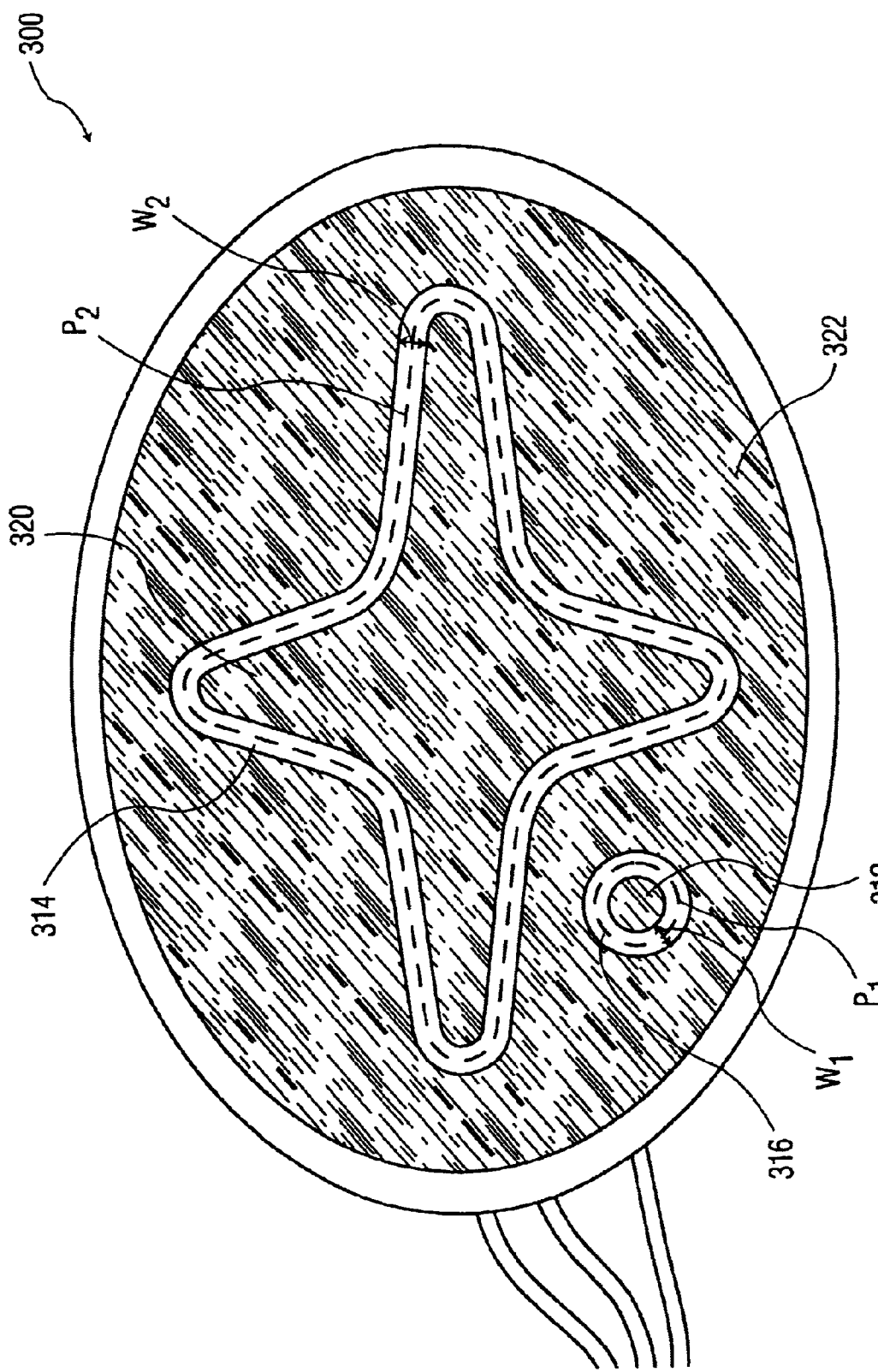
FIG. 5 is a bottom elevational view of an electrode system of another preferred embodiment wherein the electrode has three conductive elements.
Figure 6:
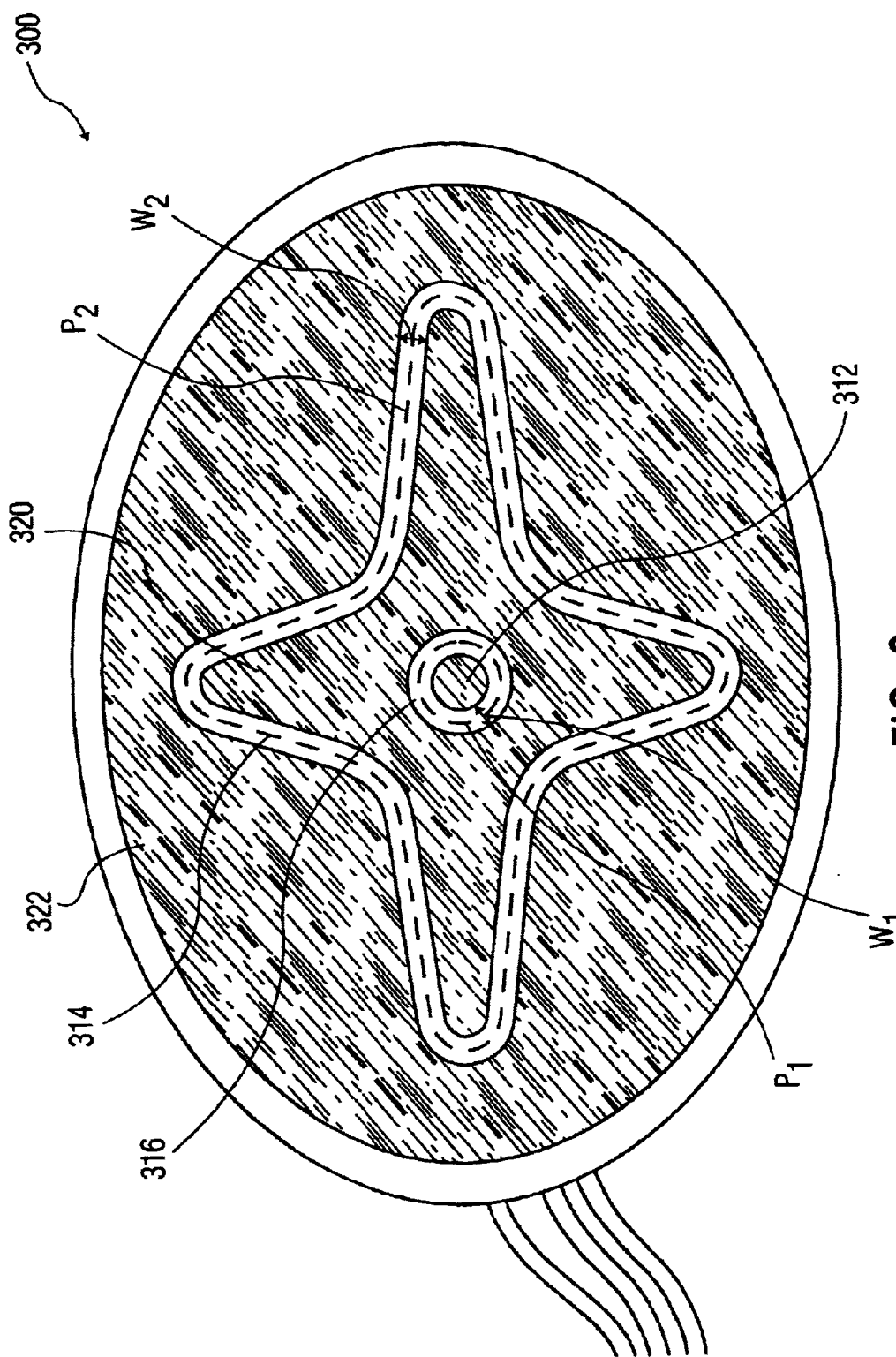
FIG. 6 is a bottom elevational view of an electrode system of another preferred embodiment wherein the three conductive elements are formed concentrically.

FIGS. 5 and 6 are bottom elevational views of alternative embodiments of an electrode of this invention. Both FIGS. 5 and 6 provide a third conductive element 312 which is used for determining the particular patient's ρ or σ. The third conductive element 312 is positioned and sized such that the determination of ρ or σ will have a minimal sensitivity to the degree of attachment of electrode pad 300. The construction of the electrode pads of FIGS. 5 and 6 is similar to the construction described in connection with the electrode pads of FIGS. 1 through 4, the only difference being the addition of an additional electrode element 312. As with the embodiments described above, the conductive contact area is from 80 to 160 cm², and more preferably 115 cm². The conductive elements 320 and 322 are separated by a gap 314. In a preferred embodiment, the gap 314 has an approximately constant width and comprises an area smaller than the combined surface areas of the conductive electrode elements 312, 320, 322; the gap 314 area being, for example, 5 to 25% of the total combined surface areas of the conductive electrode elements 320, 322.

In the embodiment shown in FIG. 6, conductive element 322 and 312 are separated by a gap 316. In a preferred embodiment, the gap 316 has an approximately constant width and comprises an area smaller than the area of gap 314; the gap 316 surface area being, for example, 5 to 25% of the area of gap 314.

In the embodiment shown in FIG. 6, conductive element 320 and 312 are separated by a gap 316. In a preferred embodiment, the gap 316 has an approximately constant width and comprises an area smaller than the area of gap 314; the gap 316 surface area being, for example, 5 to 25% of the area of gap 314.

Using an impedance based measurement, a patient's individual ρ can be calculated to provide more detailed information about the electrode pad attachment to the defibrillator. Accordingly, in using the electrode pad 300 of FIG. 5 or 6, the ρ of the patient is determined using the following equation:

Step 3A $$\rho = \frac{R_c P_1}{W_1}$$

Where ρ is the patient's skin resistivity, $R_c$ is a small-signal calibration resistance (real part of impedance) measured between elements 312 and the surrounding element (322 in FIG. 5; 320 in FIG. 6) of the gap 316, and $W_1$ is the width of the gap 316 between electrode element 312 and the surrounding element. $P_1$ is the effective perimeter of the gap 316, which is a constant value for a given geometry and may be determined either empirically or analytically. As will be appreciated by those skilled in the art, the patient's ρ may be calculated using one or both of the attached electrode pads.

Once the patient's ρ has been calculated, ρ can be used to determine the overall electrode pad attachment quality for that electrode pad by employing the following formula:

Step 3B $$\eta = \frac{\rho W_2}{P_2 R_q}$$

Where η is an indication of attachment quality of the electrode pad, ρ is the patient resistivity from step 3A. $R_q$ is a small-signal resistance (real part of impedance) measured between elements 320 and 322), $W_2$ is the gap distance 314 between the electrode element 320 and electrode element 322. $P_2$ is the effective perimeter of the gap 314 between elements 320 and 322 which is a constant value for a given geometry and may be determined either empirically or analytically.

The equation of step 3A can be calculated for each electrode pad 300 separately to determine which of the electrodes is not adhered correctly.

When the electrode pad 300 is deployed for defibrillation, the operator attaches an electrode pad to the patient's torso at each of either the anterior/anterior or the anterior/posterior position. Thereafter, the defibrillator measures $R_c$. Once $R_c$ has been measured, the defibrillator uses the information obtained from the electrode pads to determine the patient's ρ using the formula in step 3A above. The defibrillator may measure $R_c$ and calculate the ρ for both electrodes and then compare the values obtained. If the values differ significantly, then the defibrillator may determine that at least one of the electrodes is applied incorrectly. Thereafter, the defibrillator would instruct the operator to check the pad attachment. When the defibrillator was able to obtain a ρ of essentially equal magnitude from both electrodes, then the defibrillator would proceed to determine the pad attachment quality for each electrode pad by using the patient's ρ in the equation of step 3B. By calculating the pad attachment quality for each electrode pad separately, the defibrillator can determine which of the two electrodes pads are not attached in their entirety—or if, in fact, both electrode pads are not attached in their entirety.

As an alternative to the impedance based measurement discussed above, an admittance based measurement can be used. In that instance, using the electrode pad 300 of FIG. 5 or 6, the skin conductivity, σ, of the patient is determined using the following equation:

Step 4A $$\sigma = \frac{G_c W_1}{P_1}$$

Where $G_c$ is a small-signal calibration conductance representing the real part of admittance which is measured between elements 312 and the surrounding element (322 in FIG. 5, 320 in FIG. 6). As before, $W_1$ is the gap distance 316 between the electrode element 312 and the surrounding element. $P_1$ is the effective perimeter of the gap 316 between the electrode elements 312 and the surrounding element, which is a constant value for a given geometry and may be determined either empirically or analytically.

Once the patient's σ has been calculated, the η, which is an indication of attachment quality of the electrode pad can be calculated using a:

Step 4B $$\eta = \frac{G_q W_2}{\sigma P_2}$$

Where $G_q$ is the small-signal conductance measured between elements 320 and 322. Again the equation of step 4B can be used to calculate the η for each electrode pad 300 separately to determine which of the electrodes is not adhered correctly.

When the electrode pad 300 is deployed for defibrillation, the operator attaches an electrode pad to the patient's torso at each of either the anterior/anterior or anterior/posterior positions. Thereafter, the defibrillator measures $G_c$. Once $G_c$ has been measured, the defibrillator uses the information obtained from the electrode pads to determine the patient's σ using the formula in step 4A above. The defibrillator may measure $G_c$, then calculate the σ for both electrodes and then compare the values obtained. If the values differ significantly, then the defibrillator may determine that at least one of the electrodes is applied incorrectly. Thereafter, the defibrillator would instruct the operator to check the pad attachment. When the defibrillator was able to obtain a σ of essentially equal magnitude from both electrodes, then the defibrillator would proceed to determine the pad attachment quality for each electrode pad by using the patient's σ in the equation of step 4B. By calculating the pad attachment quality for each electrode pad separately, the defibrillator can determine which of the two electrode pads is not attached in its entirety—or if, in fact, both electrode pads are not attached in their entirety.

In addition to accurately determining electrode pad attachment, these electrode pad configurations can be used to detect artifact signal that may be received and/or generated by the electrode pad. Sources of artifact include, for example, mechanical movement. So, for example, when cardiopulmonary resuscitation (CPR) is performed, there is a resulting mechanical movement in the electrode pad from the chest compressions. This mechanical movement results in an electrical signal in the electrode pad. The signal is then combined with the cardiac signal received from the patient's chest and the combined signal is then transmitted to the defibrillator. As will be appreciated by those of skill in the art, the resulting combined signal can result in either a false positive or false negative determination regarding the need for a defibrillating shock. Either way, an incorrect decision could result, which could result in a defibrillating shock being administered to a patient who did not need one; alternatively an incorrect decision could result in a failure to defibrillate a patient who did require a defibrillating shock.

The electrode pads of this invention are further advantageous because they help provide a mechanism for detecting and/or removing artifact in the signal by providing an artifact reference signal. An artifact reference signal is obtained by measuring the differential voltage between any two conductive elements of the electrode pad. The actual mechanism whereby an artifact reference signal so obtained may be used to detect artifact is discussed in co-pending application entitled "Multivariable Artifact Assessment," filed concurrently herewith by David E. Snyder and Thomas D. Lyster, the content of which is incorporated herein by reference. As will be appreciated by those of skill in the art, an artifact signal so obtained may also be used to remove artifact from the corrupted signal through the application, for example, of adaptive filtering techniques (Haykin, Simon, "Adaptive Filter Theory, 3$^{rd}$ Edition," Prentice Hall, 1996).

When delivering a defibrillation or pacing energy pulse, the energy can be delivered through any of the electrode pad components or a combination thereof. In a preferred embodiment, the shock is delivered through the outer component of larger skin contact surface area than the inner component. In a second preferred embodiment, the shock is delivered through two components comprising the greatest combined skin contact area. In a third preferred embodiment, the shock is delivered through the inner component of larger skin contact area than the outer component.

As will be appreciated by those of skill in the art, the electrodes 10, 200, 300 will be bundled into sets of two electrodes when used for defibrillation and/or pacing. These sets could be organized such that each of the electrodes have the same number of conductive electrode elements. For example, two electrodes configured as shown in FIG. 5 could be bundled together as a set for use in defibrillation and/or pacing. Alternatively, an electrode as shown in FIG. 5 could be bundled in a set either with a standard defibrillation electrode (available in the prior art) or with an electrode of this invention containing a different number of conductive electrode elements. An example of this situation would be where the electrode of FIG. 5 is bundled with an electrode of, for example, FIG. 1. As will be appreciated by those of skill in the art, there are numerous combinations of electrodes possible, including configurations that include more than two electrodes. In order to avoid obscuring the invention, these combinations are not described herein since such combinations would be easily ascertainable without undue experimentation.

While this invention has been described with respect to disposable defibrillation electrode pads, it will be appreciated by those skilled in the art that the concepts may be applied to other types of electrodes, including monitoring electrodes, pacing electrodes, etc. Further, as discussed these principles may be applied to multiple electrode schemes (wherein there are more than two electrode pads).

As will be appreciated by those skilled in the art, many changes, modifications, variations and other uses and applications of the subject invention will, however, become apparent after considering this specification and the accompanying drawings which disclose preferred embodiments thereof. All such changes, modifications, variations and other uses and applications which do not depart from the spirit and scope of the invention are deemed to be covered by the invention, which is limited only by the claims which follow.

What is claimed:

1. A medical electrode pad comprising:

a substrate with an adhesive surface;

a conductive electrode island disposed on the substrate; and a conductive electrode disposed on the substrate, the conductive electrode island and the conductive electrode having a spatial relationship so that the conductive electrode is spaced apart from and surrounding the conductive electrode island;

a voltage source for supplying voltage to the conductive electrode island and the conductive electrode via a pair of conductors;

artifact reference signal detection means for detecting a voltage difference between the conductive electrode island and the conductive electrode and for determining an electrode pad attachment quality; and said pair of conductors for providing said voltage to the electrode conductive island and the conductive electrode, said pair of conductors being in communication with the substrate and coupled to the conductive electrode island and the conductive electrode, respectively, so that a first conductor of the pair of conductors is coupled to the conductive electrode island and a second conductor is coupled to the conductive electrode; and wherein said determination of electrode pad attachment quality n is a function of: (1) one of skin resistivity and a resistance between the conductive electrode island and the conductive electrode, and skin conductance and a conductance between the conductive electrode island and the conductive electrode, (2) width of the space between the conductive electrode and the conductive electrode island, and (3) an effective perimeter of space surrounding the conductive electrode island.

2. The medical electrode apparatus of claim 1 wherein the conductive electrode island and the conductive electrode have an annular spatial relationship to each other.

3. The medical electrode apparatus of claim 1, further comprising:

a second conductive electrode island disposed on the substrate such that the second conductive electrode island is spaced apart from and surrounded by the conductive electrode.

4. The medical electrode apparatus of claim 3 wherein the second conductive electrode island and the conductive electrode have an annular spatial relationship to each other.

* * * * *